(12) United States Patent
Pesika et al.

(10) Patent No.: US 11,801,332 B2
(45) Date of Patent: Oct. 31, 2023

(54) LOAD-INDUCED HYDRODYNAMIC LUBRICATION OF POROUS SUBSTRATES

(71) Applicant: The Administrators of the Tulane Educational Fund, New Orleans, LA (US)

(72) Inventors: Noshir Pesika, New Orleans, LA (US); Tushar Khosla, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 71 days.

(21) Appl. No.: 15/749,948

(22) PCT Filed: Aug. 3, 2016

(86) PCT No.: PCT/US2016/045286
§ 371 (c)(1),
(2) Date: Feb. 2, 2018

(87) PCT Pub. No.: WO2017/039924
PCT Pub. Date: Mar. 9, 2017

(65) Prior Publication Data
US 2018/0221541 A1 Aug. 9, 2018

Related U.S. Application Data

(60) Provisional application No. 62/200,507, filed on Aug. 3, 2015.

(51) Int. Cl.
*A61L 27/50* (2006.01)
*A61L 27/56* (2006.01)
(Continued)

(52) U.S. Cl.
CPC .......... *A61L 27/50* (2013.01); *A61F 2/30771* (2013.01); *A61L 27/18* (2013.01);
(Continued)

(58) Field of Classification Search
CPC .......... A61L 27/50; A61L 27/56; A61L 27/54; A61L 29/146; A61L 29/14; A61L 29/16;
(Continued)

(56) References Cited

U.S. PATENT DOCUMENTS

2003/0018353 A1* 1/2003 Yang ................. A61M 25/0045
606/194
2006/0235541 A1 10/2006 Hodorek
(Continued)

FOREIGN PATENT DOCUMENTS

| EP | 0128220 A1 | 12/1984 |
|---|---|---|
| WO | 9501139 A1 | 1/1995 |
| WO | WO-2013115868 A2 * | 8/2013 |

OTHER PUBLICATIONS

International Search Report and Written Opinion dated Jan. 24, 2017 for corresponding International Application No. PCT/US2016/045286.

(Continued)

*Primary Examiner* — Catherine A. Simone
(74) *Attorney, Agent, or Firm* — TAROLLI, SUNDHEIM, COVELL & TUMMINO L.L.P.

(57) ABSTRACT

A medical device for cooperating with a body surface of a patient includes an elastically deformable substrate having a first surface, a second surface, and a plurality of pores extending from the first surface towards the second surface to define a plurality of spaced-apart projections. A lubricant is provided in the pores. Applying a compressive force to the substrate with the body surface elastically deforms the projections to displace the lubricant out of the pores and provide hydrodynamic lubrication between the medical device and the body surface.

19 Claims, 15 Drawing Sheets

(51) Int. Cl.
  *A61L 29/14* (2006.01)
  *A61F 2/30* (2006.01)
  *A61L 27/18* (2006.01)
  *A61L 29/06* (2006.01)
  *G02B 1/04* (2006.01)
  *G02C 7/04* (2006.01)

(52) U.S. Cl.
  CPC ............... *A61L 27/56* (2013.01); *A61L 29/06* (2013.01); *A61L 29/14* (2013.01); *A61L 29/146* (2013.01); *G02B 1/043* (2013.01); *G02C 7/04* (2013.01); *A61F 2002/30354* (2013.01); *A61F 2002/30673* (2013.01); *A61F 2002/30807* (2013.01); *A61L 2400/10* (2013.01)

(58) Field of Classification Search
  CPC ........ A61L 31/146; A61L 31/16; A61L 31/14; A61L 2400/10; A61L 29/06; G02C 7/04; Y10T 428/249953; Y10T 428/249981; Y10T 428/249994; Y10T 428/249995; Y10T 428/24496
  See application file for complete search history.

(56) References Cited

U.S. PATENT DOCUMENTS

| | | | |
|---|---|---|---|
| 2014/0187666 A1* | 7/2014 | Aizenberg | A61L 15/24 523/113 |
| 2014/0328999 A1* | 11/2014 | Aizenberg | A61L 27/56 427/2.26 |
| 2015/0045909 A1* | 2/2015 | Muratoglu | C08J 9/228 623/23.72 |

OTHER PUBLICATIONS

Khosla et al., "Load-Induced Hydrodynamic Lubrication of Porous Films", ACS Applied Materials and Interfaces, vol. 7, No. 32, pp. 17587-17591, Jul. 29, 2015.

* cited by examiner

LOAD-INDUCED HYDRODYNAMIC LUBRICATION OF POROUS SUBSTRATES

RELATED APPLICATIONS

The present application is a U.S. National Stage application under 35 USC 371 of PCT Application Serial No. PCT/US2016/045286, filed on Aug. 3, 2016; which claims priority from U.S. Provisional Application Ser. No. 62/200,507, filed Aug. 3, 2015, the entirety of both of which are incorporated herein by reference.

This invention was made with Government support under Federal Grant No. CMMI-1301286 awarded by the National Science Foundation and under Contract No. NRL 6.1 WU #69-4640 awarded by ONR through the U.S. Naval Research Laboratory. The Government has certain rights in this invention.

TECHNICAL FIELD

The present invention relates generally to component lubrication and, more specifically, relates to load-induced, hydrodynamic lubrication.

BACKGROUND

Lubricants play an integral role in the operation of a number of large scale technologies including internal combustion engines, vehicles, gear systems, compressors, turbines and hydraulics, in addition to smaller scale technologies including hard disk drives and microelectromechanical systems. The main purpose of lubricants is to reduce friction and material wear. Typically, in order to reduce friction between surfaces, a liquid medium, e.g., oils containing additives or synovial fluid in joints, is used. This prevents two shearing surfaces from coming into intimate contact with each other and thereby reduces interactions such as van der Waals forces. Although significant research has gone into developing superior lubricants, relatively less work has considered engineering surfaces that exhibit low friction.

Lubrication is also important in medical applications, e.g., joint replacement and tube insertion. Cartilage is a connective tissue found in many areas of the body, including in joints between bones. It is composed of 60%-80% water, with the remainder comprised of collagen and a small volume of chondrocytes. Although there is still debate about the microstructure of collagen, it is agreed that the cartilage has an array of open and parallel tubular pores in axial and lateral directions.

Cartilage is surrounded by an extracellular fluid called synovial fluid, which runs through the cartilage pores to provide nutrition to the cells. Cartilage has a low coefficient of friction of about 0.005-0.0423. Cartilage and synovial fluid work synergistically to make joint lubrication efficient. The load applied on cartilage is supported by the extracellular matrix, which uses the charged species to create osmotic pressure to hydrate the cartilage. During movement at high shear velocities, the hydrodynamic lubrication regime dominates.

It has been shown that the measured friction force in cartilage is inversely proportional to the pressure of the synovial fluid, which is regulated by the pore matrix. It is believed that a thick, pressurized layer of synovial fluid separates the shearing cartilage surfaces and is responsible for ultra-low friction. Synovial fluid is rich in boundary lubricants: hyaluronic acid, surface active phospholipids, and superficial zone proteins. These lubricants act as a sacrificial layer during shear at slow speeds and therefore need to be replaced continuously. In order to successfully replicate such a system, it is important to consider both the properties of the lubricant and the mechanical and structural properties of the sliding surfaces.

SUMMARY

In accordance with an aspect of the present invention, a medical device for cooperating with a body surface of a patient includes an elastically deformable substrate having a first surface, a second surface, and a plurality of pores extending from the first surface towards the second surface to define a plurality of spaced-apart projections. A lubricant is provided in the pores. Applying a compressive force to the substrate with the body surface elastically deforms the projections to displace the lubricant out of the pores and provide hydrodynamic lubrication between the medical device and the body surface.

In another aspect of the present invention, a method of fabricating a medical device for cooperating with a body surface of a patient includes forming an elastically deformable substrate having a first surface, a second surface, and a plurality of pores extending from the first surface towards the second surface to define a plurality of spaced-apart projections. Air is removed from the pores. A lubricant is deposited within the pores such that applying a compressive force to the substrate with the body surface elastically deforms the projections to displace the lubricant out of the pores and provide hydrodynamic lubrication between the medical device and the body surface.

In another aspect of the present invention, a device for cooperating with a force-producing component includes an elastically deformable substrate having a first surface, a second surface, and a plurality of pores extending from the first surface towards the second surface to define a plurality of spaced-apart projections. A lubricant is provided in the pores. Applying a compressive force to the substrate with the component elastically deforms the projections to displace the lubricant out of the pores and provide hydrodynamic lubrication between the device and the component.

In another aspect of the present invention, a method of fabricating a device for cooperating with a force-producing component includes forming an elastically deformable substrate having a first surface, a second surface, and a plurality of pores extending from the first surface towards the second surface to define a plurality of spaced-apart projections. Air is removed from the pores. A lubricant is deposited within the pores such that applying a compressive force to the substrate with the component elastically deforms the projections to displace the lubricant out of the pores and provide hydrodynamic lubrication between the device and the component.

The present invention discloses methods and devices for continuous lubrication of porous polymer surfaces. The results herein demonstrate the tribological properties and mechanisms of porous polymer surfaces under applied loads in aqueous media. The lubrication regime may be changed from boundary lubrication to hydrodynamic lubrication even at relatively low shearing velocities by the addition of pores to a compliant polymer. The compressed, pressurized liquid in the pores produces a repulsive hydrodynamic force as it extrudes from the pores. The presence of the fluid between two shearing surfaces results in low coefficients of friction ($\mu \approx 0.31$). The coefficient of friction is reduced further by using a boundary lubricant. A range of applied loads and shear velocities are evaluated to demonstrate the potential application of the presently-disclosed materials as joint replacement devices.

Other objects and advantages and a fuller understanding of the invention will be had from the following detailed description and the accompanying drawings.

DETAILED DESCRIPTION

Figure 1A:
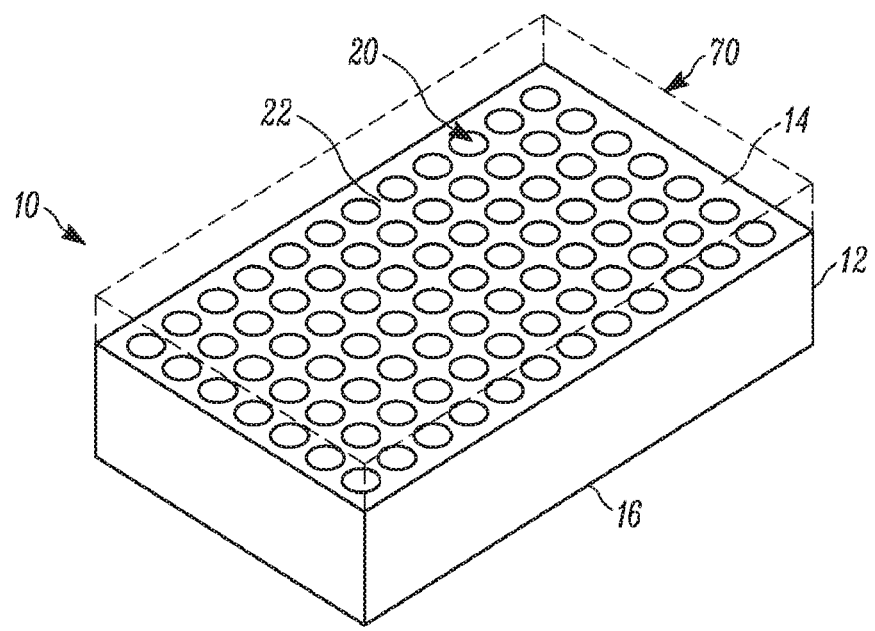
FIG. 1A is an isometric view of an example lubrication device in accordance with the present invention.
Figure 1B:
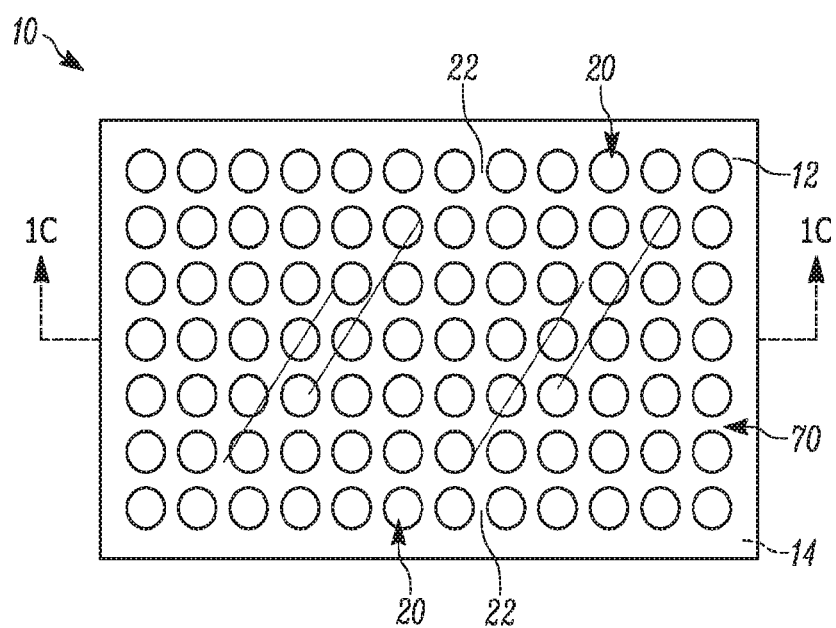
FIG. 1B is a top view of the device of FIG. 1A.
Figure 1C:
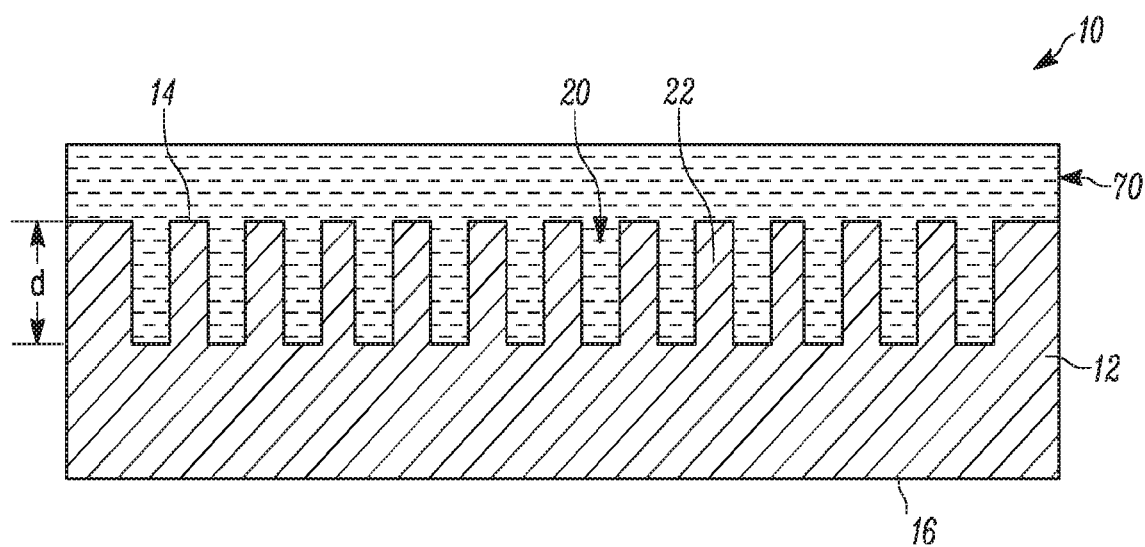
FIG. 1C is a section view of the device of FIG. 1B taken along line 1C-1C

The present invention relates generally to component lubrication and, more specifically, relates to load-induced, hydrodynamic lubrication. FIGS. 1A-1C illustrate an example lubrication device 10 in accordance with the present invention. The device 10 includes a substrate 12 and a lubricant 70 that cooperates with the substrate to produce hydrodynamic lubrication.

The substrate 12 is formed from an elastically deformable/compliant material having a Young's Modulus of about 0.1 MPa to about 100 MPa. Example materials for the substrate include polydimethylmethoxysilane, cross-linked polydimethylmethoxysilane, hydrogels, polyvinylalcohol, and biological or biologically compatible materials such as collagen.

The lubricant 70 is formed from one or more incompressible liquids each having a viscosity of about $1 \times 10^{-4}$ Pa-s to about 10 Pa-s. Example lubricants 70 include, but are not limited to, water soluble liquids such as sodium dodecyl sulfate (SDS), non-water soluble liquids, Newtonian liquids such as oil and water, one or more biocompatible surface active agents such as hyaluronic acid, phospholipids, glycerol, hydrogel, liquid polymers, multiphase systems such as solids dispersed in a liquid, and combinations thereof.

The substrate 12 includes a first surface 14 and a second surface 16. As shown, the substrate 12 is planar and, thus, the surfaces 14, 16 are substantially parallel to one another. A series of pores or openings 20 extends from the first surface 14 towards the second surface 16, terminating prior to reaching the second surface and defining a series of projections 22. The projections 22 therefore cooperate to form the contour of the first surface 14.

The pores 20 can have a round or circular shape (as shown) or have polygonal shapes (not shown). The pores 20 can all have the same shape or different shapes from one another. Each pore 20 has a depth d from the first surface 14 on the order of about about 50 nm to about 100 µm. Although the pores 20 are illustrated in FIG. 1C as having the same depth d, it will be appreciated that the pores 20 can have different depths d from one another. Each pore 20 can have a diameter ranging from about 50 nm to about 100 µm with the diameters being the same or different from one another. The diameter of each pore 20 can be constant or variable.

The pores 20 are arranged about the substrate 12 in a predetermined manner. As shown, the pores 20 are substantially evenly spaced in a grid-like array about the first surface 14. It will be appreciated that the pores 20 could be arranged in a different symmetrical arrangement or arranged asymmetrically.

Figure 2A:
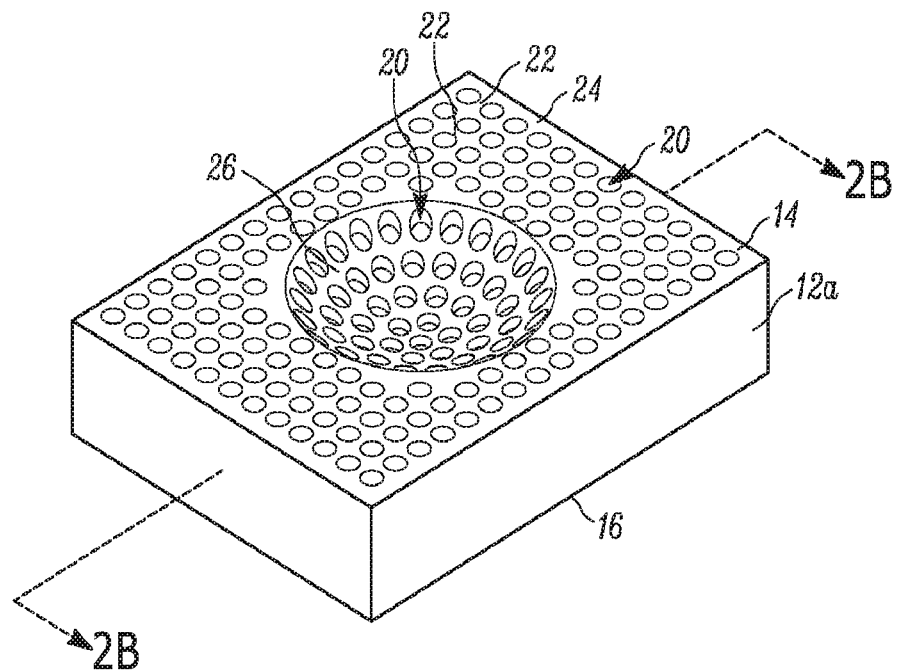
FIG. 2A is an isometric view of an alternative configuration for a substrate of the device of FIGS. 1A-1C.
Figure 2B:
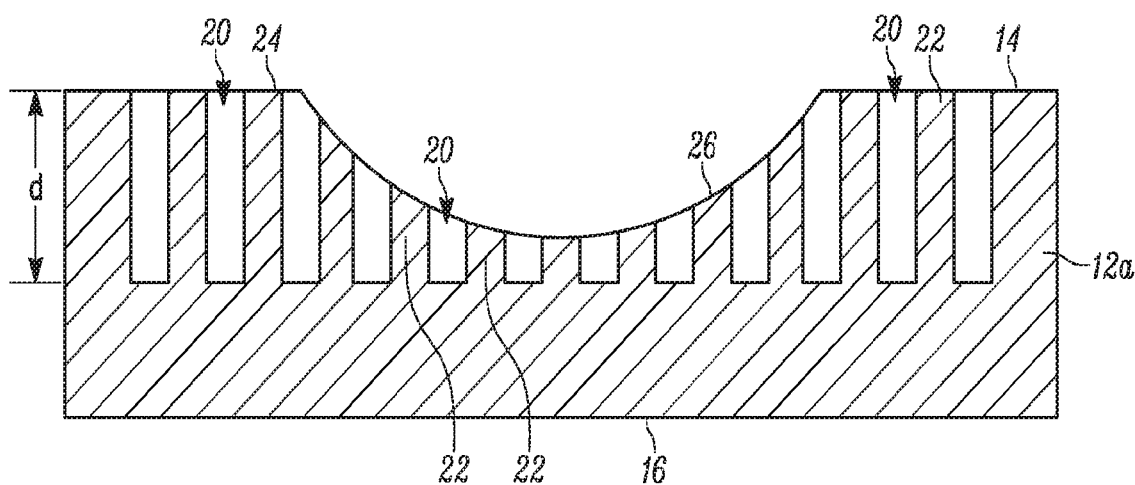
FIG. 2B is a section view of the device of FIG. 2A taken along line 2B-2B.

FIGS. 2A-2B illustrate an alternative substrate 12a in accordance with the present invention. The substrate 12a includes a first surface 14 having a first portion 24 and a second portion 26. The first portion 24 is planar and the second portion 26 is non-planar. As shown, the second portion 26 is arcuate, e.g., concave. To this end, the heights of the projections 22 defining the second portion 26 are varied to form the second portion in the desired shape. Due to the arcuate shape of the second portion 26, the pores 20 extending through the second portion are shallower than the pores extending through the first portion.

It will be appreciated that the projections 22 can be varied in size, shape, and location to define one or more second portions 26 having any desired shape(s) or contour(s), e.g., oval, elliptical, circular or polygonal. The first portion 24 can also be omitted.

Figure 3A:
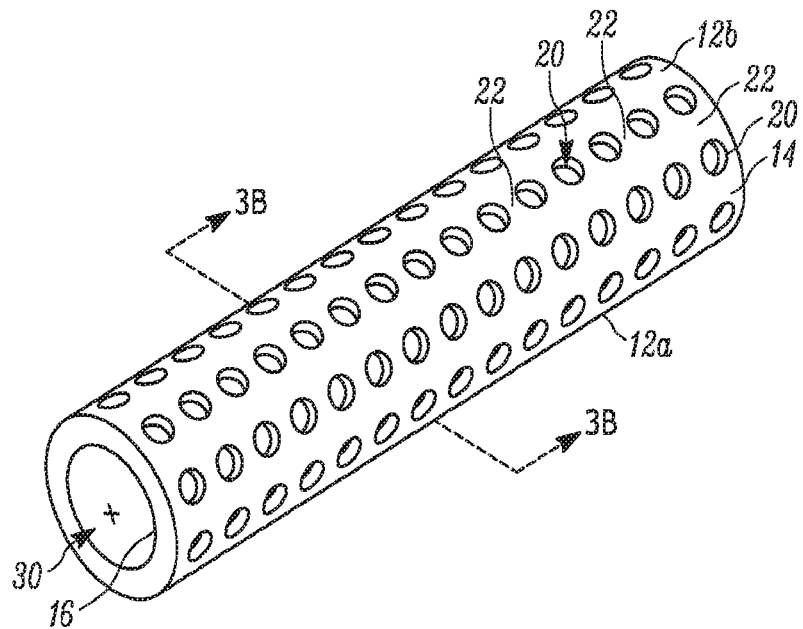
FIG. 3A is an isometric view of another example lubrication device in accordance with the present invention.
Figure 3B:
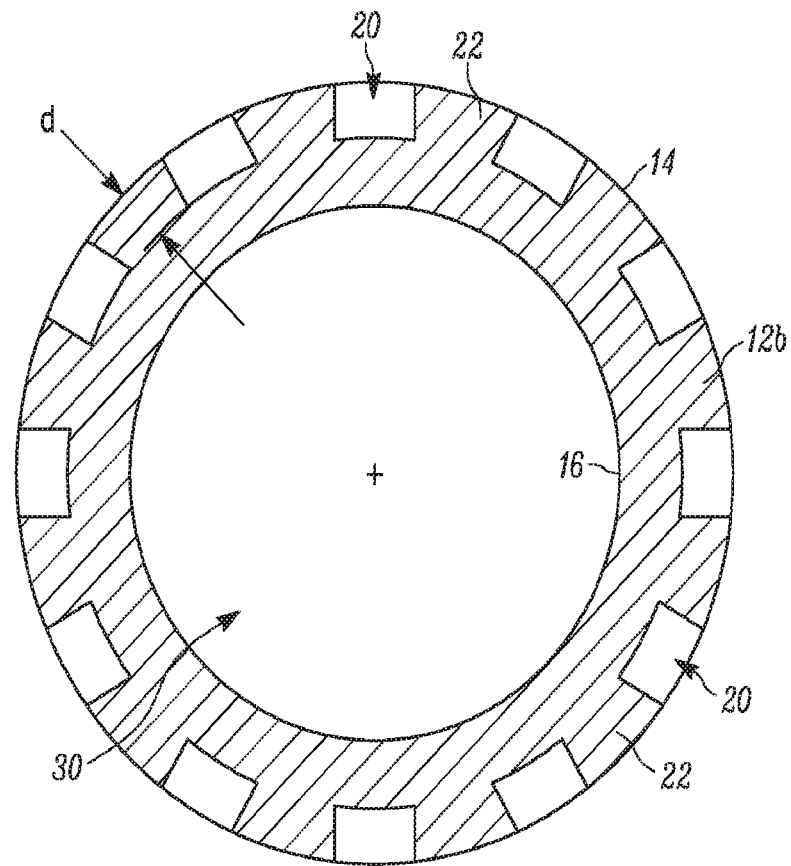
FIG. 3B is a section view of the device of FIG. 3A taken along line 3B-3B.
Figure 4A:
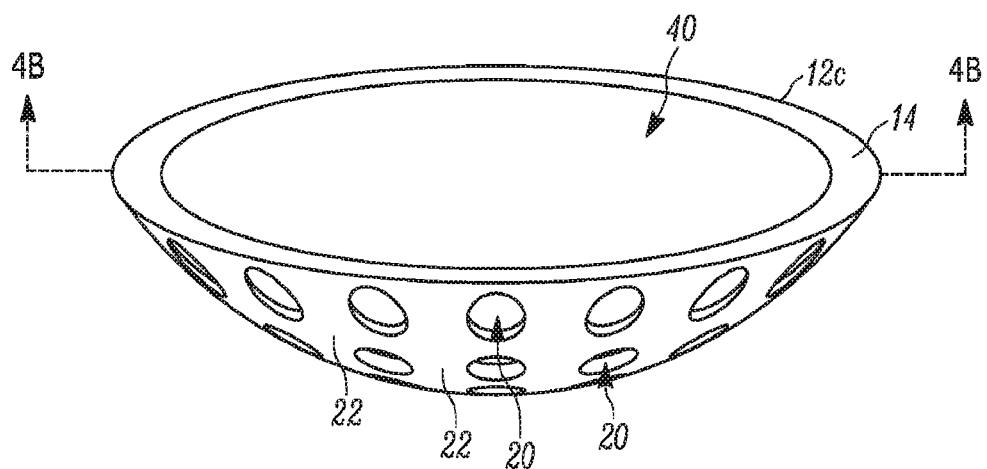
FIG. 4 is a front view of another example lubrication device in accordance with the present invention.
Figure 4B:
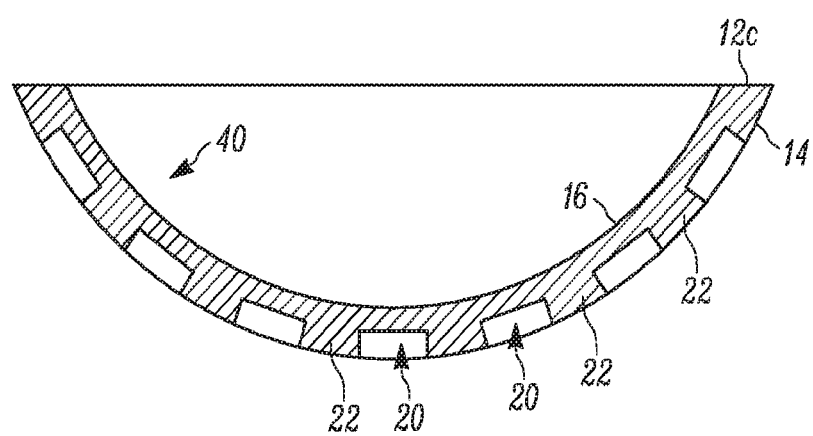

FIGS. 3A-4 illustrate alternative substrates 12b, 12c in accordance with the present invention. The substrate 12b in FIGS. 3A-3B is tubular such that both the first surface 14 and the second surface 16 are round, e.g., circular or elliptical. As shown, the first and second surfaces 14, 16 are concentric with one another. The second surface 16 defines a longitudinally extending passage 30 extending the entire length of the substrate 12v. The pores 20 extend radially inward towards passage. The substrate 12c in FIG. 4 is arcuate, e.g., concave, and defines a chamber 40. In one instance, the substrate 12c mimics the shape of a contact lens.

The substrates 12-12c of the present invention can be used for or incorporated into healthcare or personal care applications such joint replacement devices (the devices 12-12a), intubation or catheterization tubes (the device 12b), contact lenses (the device 12c), and any other medical device where lubrication is desirable. Alternatively, the devices 12-12c can be incorporated into machinery with shearing surfaces or in any other industrial application.

The substrates 12-12c of the present invention can be formed in several ways. In one instance, a negative mold is formed having a plurality of pores. The negative mold can be formed by, for example, patterning using photolithography. The soft compliant material(s) forming the substrate 12-12c is deposited in the negative mold, solidified as a unitary structure, and then removed from the negative mold. A vacuum can be applied to the pores 20 to remove any air therefrom. The lubricant 70 is then deposited within the vacuumed pores 20 and overlying the first surface 14 of the substrate 12-12c to form the device 10 of FIG. 1A.

Alternatively, the substrate 12-12c is initially molded or otherwise formed without pores 20. After the substrate 12-12c solidifies, the pores 20 are formed in the substrate by at least one of punching, pressing, depressing, embossing, embedding, puncturing, and squeezing in accordance with the present invention. The pores 20 can then be vacuumed free of air and the lubricant 70 deposited in the air-free pores as previously described.

Figure 5:
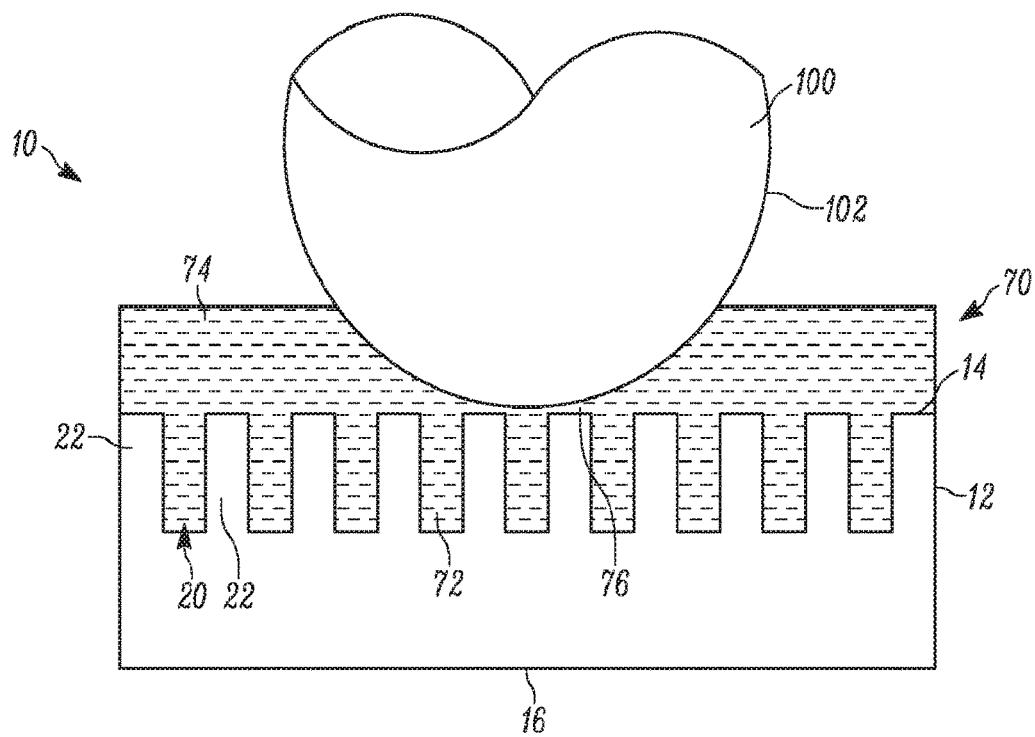
FIGS. 5-6 are schematic illustrations of the lubrication device of FIGS. 1A-1C interacting with a force-producing component.
Figure 6:
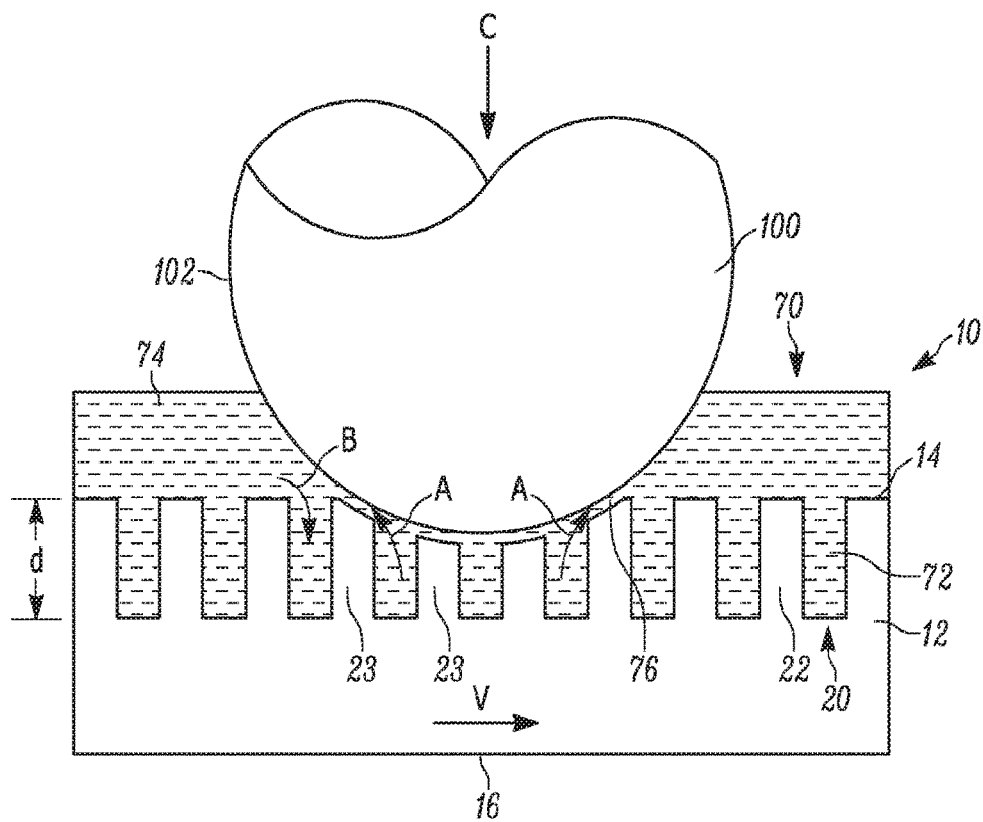

FIGS. 5-6 illustrate operation of the device 10 with the substrate 12 and a force-producing component or member 100. Depending on the application, the force-producing component 100 can constitute a piece of machinery, industrial equipment or a body surface of a patient, e.g., femoral head, humeral head, esophagus, trachea, artery, vein, urethra or eye [more specifically eye and/or eyelid]. The appropriately shaped substrate 12-12c is chosen based on the configuration of the force-producing component 100. For example, although the force-producing component 100 is shown as being round it will be appreciated that when the force-producing component constitutes the inner surface of a patient's body lumen or cavity, e.g., esophagus, trachea, artery, vein, urethra or any other body lumen where procedures such as catheterization or tube insertion is desirable, the tubular substrate 12b is used. The passage 30 therefore acts as a fluid delivery and removal means and the first surface 14 abuts the inner surface of the body lumen. Similarly, the substrate 12c is used to accommodate a human eye (not shown) in the chamber 40 such that the first surface 14 abuts the patient's cornea.

In use, a portion 72 of the lubricant 70 is provided in the pores 20 and a portion 74 extends over the first surface 14. The force-producing component 100 is aligned with the projections 22 and brought into contact with the lubricant 70 such that a thin fluid layer 76 extends between an outer surface 102 of the force-producing component and the projections 22 (FIG. 5). The device 10 of the present invention is configured such that the thin film layer 76 is maintained between the projections 22 and force-producing component 100 when the force-producing component applies a compressive load C to the substrate 12 and/or shears over the first surface 14 at a velocity V (FIG. 6). The velocity V can be constant or variable.

As shown in FIG. 6, when the force-producing component 100 compresses the substrate 12, some projections 23 elastically deform, e.g., compress, tilt, and move relative to one another. As a result, the lubricant portion 72 is pressurized and extruded/forced out of the pores 20 towards the force-producing component 100. As the force-producing component 100 slides across, rotates, and/or tilts relative to the substrate 12, the projections 23 adjacent to it extrude pressurized lubricant 72 out of the pores 20 as indicated by the arrow A.

At the same time, projections 22 that become misaligned from the moving force-producing component 100 are relieved of stress, return to their initial, unstressed condition allow lubricant 70 to flow back into the pores 20 unpressurized as indicated by the arrow B. This extruding and refilling cycle A, B occurs continuously during relative movement between the force-producing component 100 and the substrate 12 such that the thin film fluid layer 76 is constantly replenished. Consequently, hydrodynamic lubrication is maintained between the force-producing component 100 and the substrate 12 during relative movement therebetween.

In fact, the construction of the substrate 12, namely, the elastically deformable projections 22, 23 defined by the porous first surface 14, allows the lubricant 70 to provide continuous, hydrodynamic lubrication between the components 10, 100. This holds true even at low shear velocities V where one would typically expect boundary lubrication to dominate for flat surfaces.

It is desirable that the thickness of the lubricant 70 be greater than any surface asperities of the first surface 14 to ensure continuous spacing of the outer surface 102 from the projections 22. To this end, as the first surface 14 shears, the boundary lubricant 70 must be continuously replaced. At high shear velocity, the sliding surfaces 14, 102 enter the hydrodynamic lubrication regime. In this regime, a thicker, pressurized layer of liquid exists between the shearing surfaces 76, decreasing friction. Due to the thicker layer, the two sliding surfaces 14, 102 are never in contact, thereby reducing surface wear.

Example 1

Materials and Methods

Conventional photolithography was used to create pillars of Su-8 photoresist (MicroChem) in a square lattice on silicon wafers (Test grade, University wafers). The latter was then used as a mold to obtain the final porous polymer substrate samples out of PDMS (Sylgard 184, Dow Corning). PDMS was selected because it is stable in aqueous media, is biocompatible, and has a compressive modulus similar to cartilage (0.8-2 MPa). The PDMS samples were provided with various patterns of pore size and spacing to demonstrate the potential of reducing friction against other shearing surfaces through a load-induced hydrodynamic lubrication mechanism.

In order to facilitate removal of the PDMS from the mold, the silicon wafers with Su8 patterns were treated with Octadecyltrichlorosilane (OTS) (Sigma Aldrich). OTS treatment was done by immersing the wafers into a 100 μL OTS per 100 mL pentane (HPLC grade, Pharmaco-Aaper) solution for about 5 minutes. The wafers were then rinsed with pure pentane, DI water, and ethanol to remove excess OTS, followed by drying under Nitrogen (UHP, Airgas). The PDMS samples were cured for about 24 hours at 60° C.

A Universal Material Tester (UMT-2, CETR) was used to apply a fixed preload to the PDMS sample and measure the friction forces between a glass lens (27420, Edmund Optics) with a radius of curvature of 6 mm and the porous PDMS surfaces. To ensure that the surfaces of both the glass lens and the PDMS sample were clean and that water penetrated into the inherently hydrophobic PDMS pores, the probe and all PDMS samples were exposed to air plasma for about 60 seconds. The porous PDMS surfaces were then submerged in water under vacuum for approximately 20 seconds to remove the air from the pores and to replace it with water. Throughout the experiments, the samples were kept submerged in water to compensate for losses due to evaporation. Stock solutions of SDS (Sigma Aldrich) were made at various concentrations to study the effect of adding a boundary lubricant. All chemicals used were used as received.

Results and Discussion

The friction force between the PDMS sample and a spherical glass probe was measured while shearing a fixed distance at a constant speed. Similar to the "weeping" lubrication mechanism of cartilage, the pressurized liquid supported most of the load, resulting in a significant reduction in friction.

Figure 7:
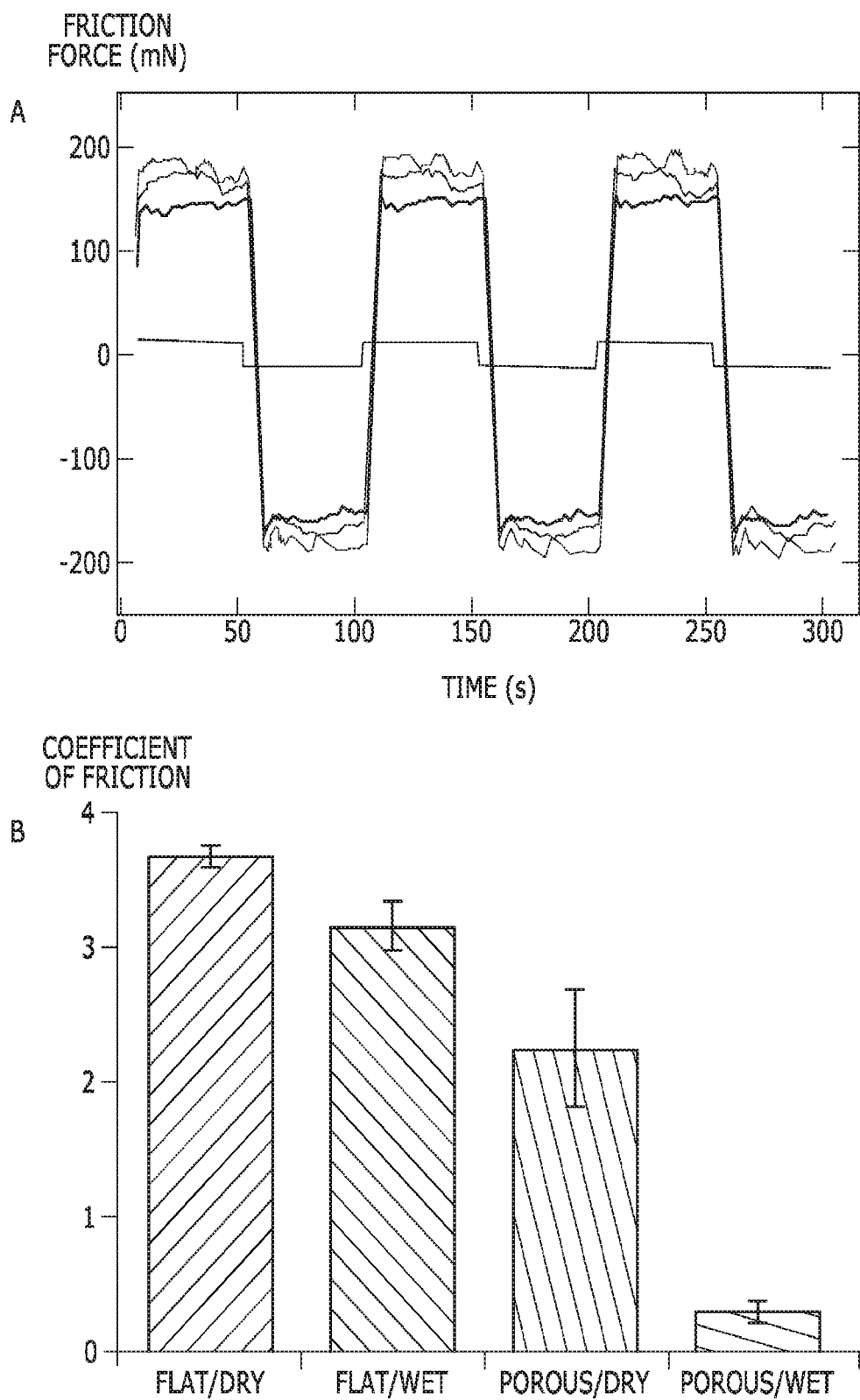
FIG. 7A is a plot illustrating friction force vs. time while shearing a glass probe on a PDMS surface for various test conditions.
FIG. 7B is a plot illustrating the average coefficient of friction between a spherical glass probe and the PDMS surface under various conditions.

The COF between the PDMS sample and the glass probe were compared by applying a 49 mN (5 g) load and shearing at a constant speed of 100 μm/s under four test conditions: (1) flat PDMS sample with a glass lens under dry conditions, (2) flat PDMS sample with a glass lens under aqueous conditions, (3) porous PDMS sample with a glass lens under dry conditions, and (4) porous PDMS sample having various pore diameters and spacing with a glass lens under aqueous conditions. Each set of experiments was performed five times. Friction force vs. time plots during shearing for each case are shown in FIG. 7A. The average coefficient of friction in each case is shown in FIG. 7B.

The first set (1) of experiments consisted of shearing a spherical silica surface against a flat PDMS surface under dry conditions. The Young's Modulus of the PDMS surface is 1~2 MPa, which allows for relatively large projection deformations when small normal loads are applied. The high coefficient of friction of around 3.68 is consistent with the large contact area, resulting from relatively large projection deformations and the fact that both component surfaces had a high surface energy due to plasma treatment. Under the aqueous conditions in set (2), the water acted as a boundary lubricant, which is evident in that the COF was reduced slightly from 3.7 to 3.16.

The decrease in the COF to 2.25 in sample set (3), which uses porous PDMS samples, can be explained by the modified Amontons' law:

$$Fx = \mu L + \Gamma A$$

where F is the friction force at an applied load L, $\Gamma$ is the shear stress, A is the true area of contact and $\mu$ is the friction coefficient. The introduction of pores on the first surface reduced the actual amount of polymer in contact with the probe, thereby reducing both the apparent and true area of contact between the two sliding surfaces.

The drastic decrease in the COF to a value of 0.31 under the aqueous conditions for the patterned, porous PDMS in set (4) cannot be explained solely by the boundary lubrication contribution of water. As the silica probe under an applied load sheared against the porous PDMS surface, water was extruded from the pores, resulting in a repulsive hydrodynamic force as the water drained. The draining water maintained a separation gap between the silica and porous PDMS surfaces, which changed the lubrication regime from boundary lubrication to hydrodynamic lubrication. As the probe moved, the pores on the trailing side no longer experienced a compressive local stress, elastically regaining their original shape, and allowing water to flow back into the pores. This mechanism ensures that the samples had a low coefficient of friction for an extended period of time—as long as the water is present.

Figure 8A:
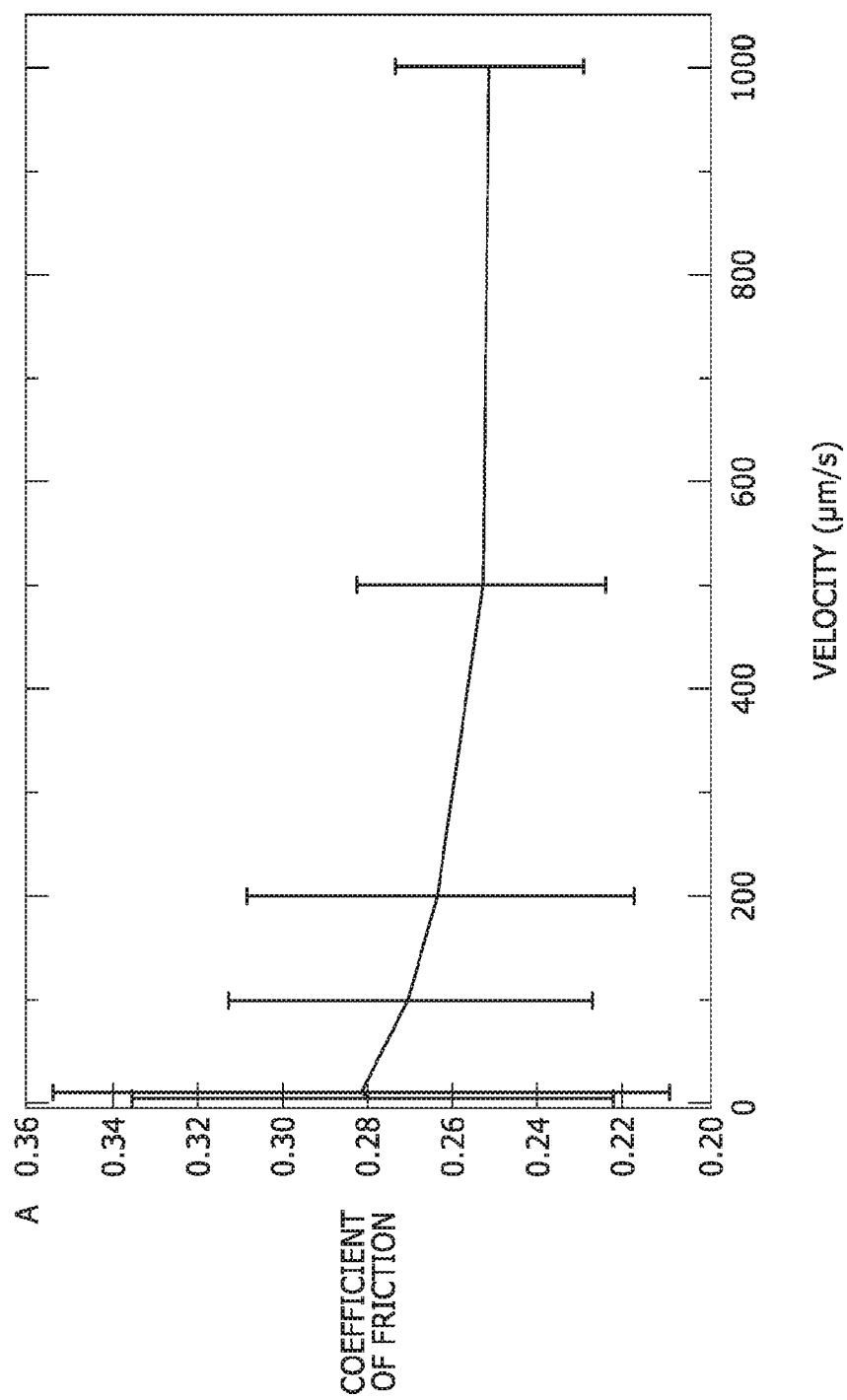
FIGS. 8A-8B are plots illustrating the coefficient of friction between a spherical glass probe and a porous PDMS surface as a function of shear velocity and applied load.
Figure 8B:
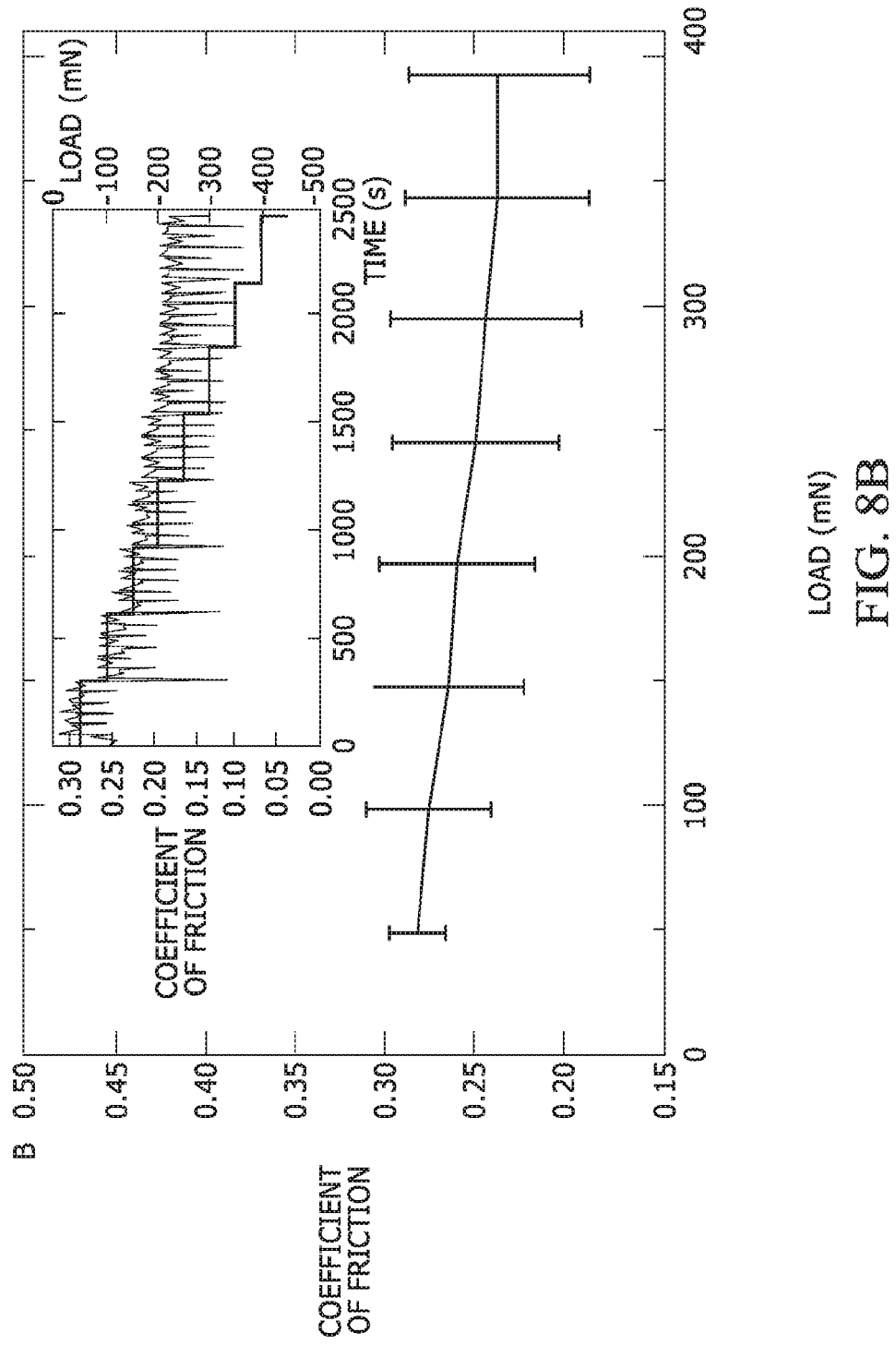

To show that hydrodynamic lubrication could be exploited over a range of velocities, a PDMS sample with pores 40 μm deep, 20 μm in diameter, and spaced 20 μm apart end-to-end was tested over speeds ranging from 5 μm/s to 1000 μm/s under aqueous conditions. The same PDMS sample was used to study the effect of increasing load on the coefficient of friction in aqueous conditions by increasing the load from 49 mN (5 g) to 392 mN (40 g). FIGS. 8A-8B summarize the results of both these test conditions, showing that the friction coefficient is low for the entire range of shear velocities. With respect to the influence of applied load, a slight decrease in the coefficient of friction was observed from 0.28 to 0.26 with increasing loads. This decrease in friction is small and is more significant at lower loads. This reduction in friction may be attributed to the fact that PDMS is compliant and therefore more pores contributed as loading increased due to an increase in contact area. These results demonstrate that the system provides low friction over a wide range of shear velocities and applied loads.

Figure 9:
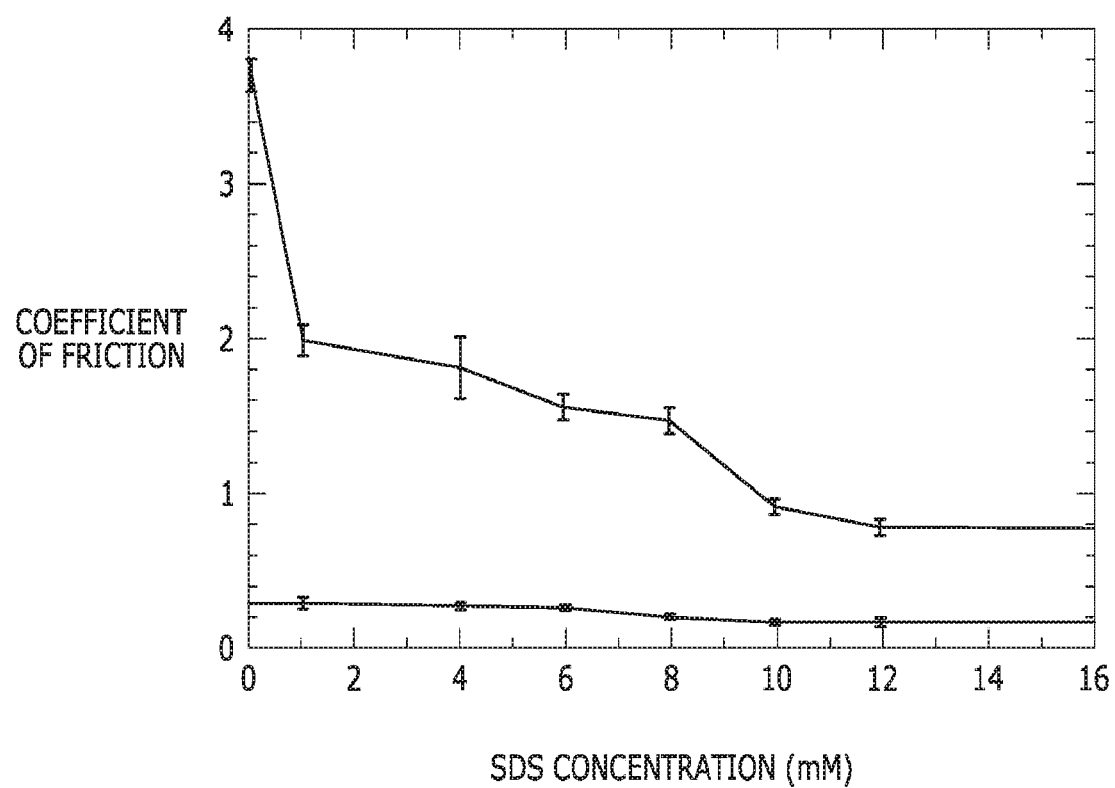
FIG. 9 is a plot illustrating the coefficient of friction as a function of SDS concentration for a flat surface of PDMS compared to a textured surface of PDMS (bottom line).

In the sample sets discussed above, the coefficient of friction, although lower than that of a flat, non-porous sample under similar conditions, is still much higher than that of cartilage. In order to further reduce friction, SDS was used as a boundary lubricant. FIG. 9 shows the effects of using various concentrations of SDS for both flat and textured/porous polymer samples. These results show that SDS at a very small concentration of 1 mM acts as a boundary lubricant for a flat surface but has no significant effect on the textured surface. This is not surprising because the flat surface produced a larger contact area, and therefore boundary lubricants are expected to have a larger effect. However, by increasing the concentration of SDS, the contribution of the boundary lubricant was apparent even in the textured samples, reducing friction at regions where the probe made contact with the textured PDMS surface and resulted in a lower COF.

Figure 10:
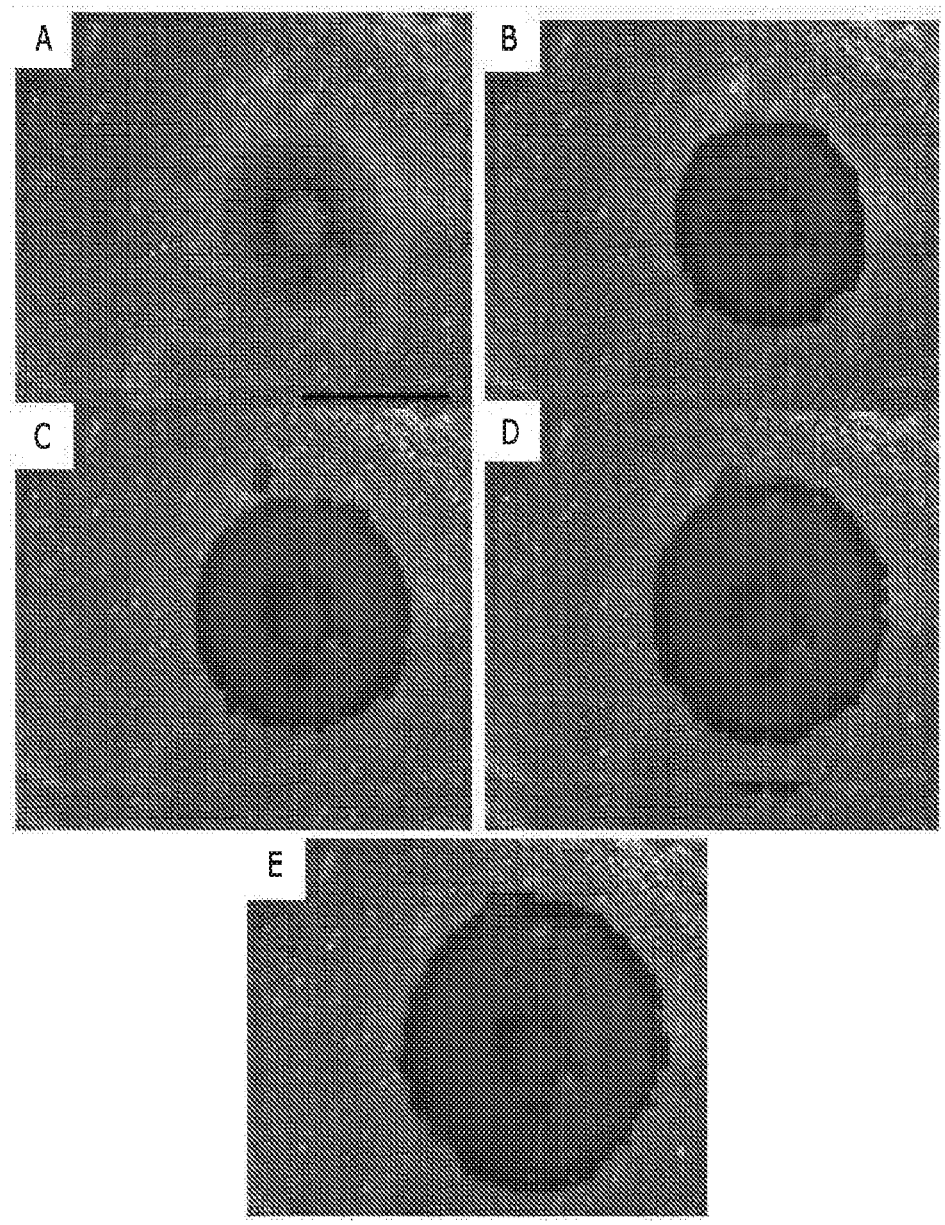
FIGS. 10A-10E are optical images of the area of contact between a glass probe and a textured PDMS sample.

FIG. 10 shows optical images of the area of contact between a glass probe and a textured PDMS substrate at compressive preloads of (A) 45 mN, (B) 135 mN, (C) 225 mN, (D) 315 mN, and (E) 405 mN. The glass probe was coated with blue food color (McCormick). The images were captured using an OPTIM Zoom 70 high magnification camera showing the bottom view of the transparent PDMS sample. The sample consisted of 20 μm wide pores spaced 15 μm from each other end-to-end. The area of contact increased as the applied load increased from approximately 0.95 mm$^2$ at 45 g to 2.88 mm$^2$ at 405 g. These images support the observations made in FIG. 8B that showed a decrease in COF upon increasing the applied load.

Overall, these results showed that by creating pores in compliant polymer surfaces, hydrodynamic or mixed lubrication can be exploited even at low shear speeds. Low friction can be maintained for a wide range of shear velocities and applied load. The addition of a boundary lubricant can further reduce friction for a relatively low applied load and shear velocity. This effect can persist over a wide range of shear velocities and applied loads. In other words, it can be demonstrated that by creating pores in a compliant PDMS surface, hydrodynamic (or mixed) lubrication can be induced in aqueous conditions, even at low shearing speeds where boundary lubrication would typically dominate.

Example 2

Figure 11:
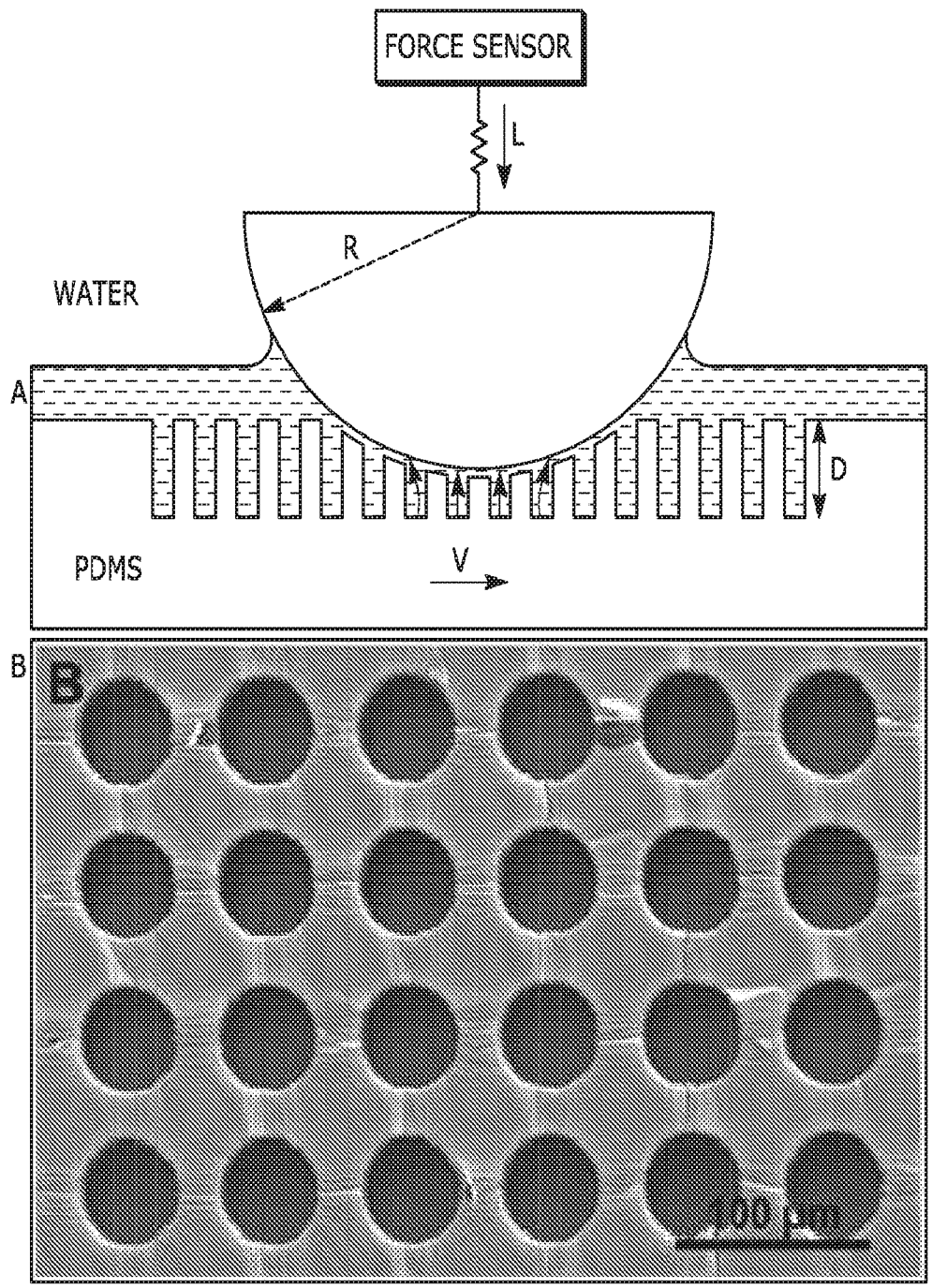
FIG. 11A is a schematic illustration of the experimental setup used to quantify the lubrication between a spherical glass probe and a compliant polymer.
FIG. 11B is an SEM image of the top view of a porous PDMS sample.

FIG. 11A shows a schematic illustration of the experimental setup used in the example to quantify the lubrication between a spherical glass probe and a compliant polymer under an applied load L and shearing velocity V. An SEM image of the top view of the porous PDMS sample used is shown in FIG. 11B. The porous PDMS sample had pores 50 µm in diameter spaced 25 µm apart. The pores were 30 µm in depth.

We hypothesized that when a localized normal load was applied on these soft polymer surfaces, pressurized water was extruded from the pores, thereby forming a water layer between the two sliding surfaces. The latter lubrication mechanism, which was termed load-induced hydrodynamic lubrication (LIHL), resulted in relatively low friction forces ($\mu=0.31$), much lower than that between glass and flat PDMS under similar conditions ($\mu=3.16$). The design of such textured surfaces was inspired by the weeping lubrication mechanism of the cartilage, which works synergistically with synovial fluid to facilitate joint movements.

In this study, we further investigated the effect of various parameters that influence LIHL of porous polymers composed of PDMS in aqueous conditions. Specifically, the effects of (i) the radius of curvature R of a spherical probe, (ii) different probe materials, (iii) the Young's Modulus of the PDMS substrate sample, and (iv) the depth D of the sample pores on the lubrication properties. A PDMS sample with a non-uniform pattern of pores, i.e., varied pore spacing and dimensions, was also used in the study to verify the importance of pattern uniformity. A systematic study of these factors enhances our understanding of the underlying mechanisms for LIHL of porous polymers and potential improvements in design could lead to creating surfaces with ultra-low friction.

Fabrication of Porous PDMS Samples

PDMS samples were made by molding from patterned silicon wafers. Photolithography was used to create patterns on silicon wafers (test grade, University Wafers) using SU-8 photoresist (MicroChem). Different viscosities of SU-8 (i.e., SU-8 3050, SU-8 3025 and SU-8 3005) and spin conditions were selected according to the protocol provided by MicroChem to obtain different film thicknesses on silicon wafers. To facilitate demolding of PDMS, the silicon wafers were coated with Octadecyltrichlorosilane (OTS, Sigma-Aldrich) by immersing the wafers in a solution of 100 µl OTS per 100 ml of pentane (HPLC grade, Pharmaco-Aaper) for 2 minutes. The wafers were then washed with pentane, DI water and ethanol to remove excess OTS, and then dried with nitrogen (UHP, airgas). Sylgard 184 (Dow Corning) was then poured onto the silicon master mold. The PDMS samples were cured in an oven at 60° C. for 24 hours after which the porous PDMS was peeled off from the silicon mold. An optical profilometer (Zygo) was used to characterize of the depth of the channels. All porous PDMS samples consisted of a 10:1 polymer to crosslinker ratio. Unless otherwise noted, SEM images of the porous PDMS samples were obtained using Hitachi 4800 High-resolution Scanning Electron Microscope.

Friction Force Measurements

A universal materials tester (UMT-2, CETR) was used to measure the friction force between the shearing probe and the PDMS sample under various test conditions. A typical experiment consisted of applying a pre-load and shearing the two surfaces at a constant speed (0.20 mm/s or 0.40 mm/s) The probe was connected to the force sensor (FL, CETR) through a spring (spring constant $K_{FL}$=520 N/m). Various borosilicate glass lenses of different curvature (Edmund Optics), 0.25" diameter steel, ceramic and plastic balls (McMaster-Carr) were used as probes to shear against the PDMS samples. All the probes and PDMS samples were cleaned with air plasma for 60 s before starting the experiment. To ensure that water penetrated inside the hydrophobic pores of PDMS, the cleaned PDMS samples were immediately submerged in water under vacuum for approximately 20 s to replace the air from the pores with water. Throughout the experiments samples were submerged in water to compensate for any loss through evaporation. All chemicals and materials were used as-received.

Results

Figure 12:
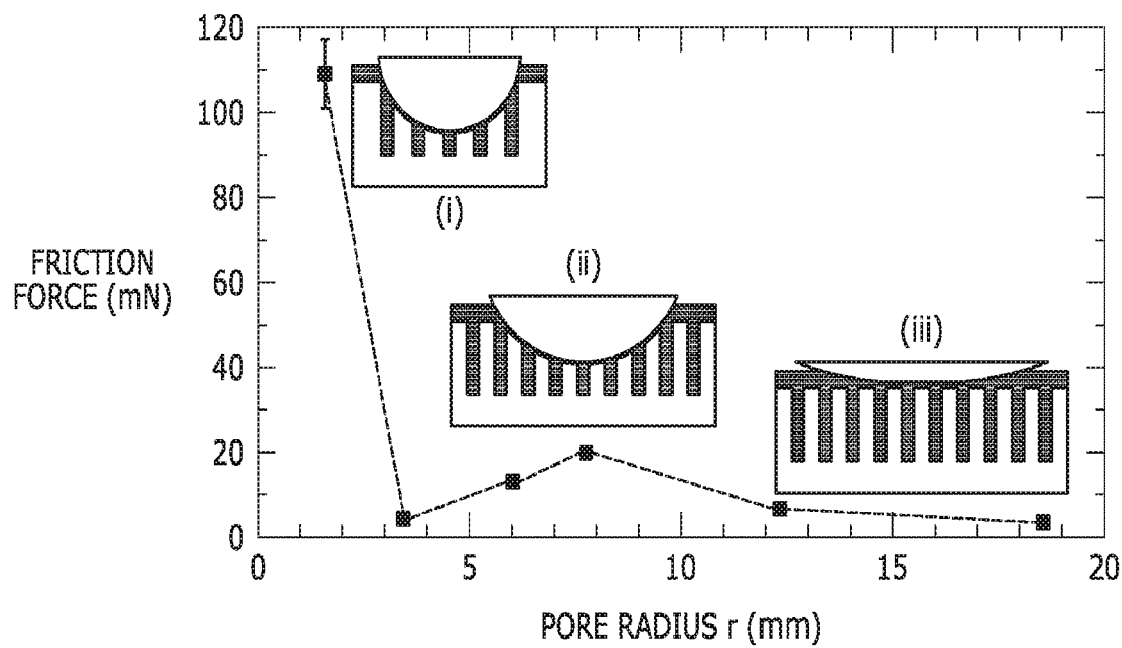
FIG. 12 is a plot of the friction force between spherical glass probes of different radii of curvature.

FIG. 12 shows a plot of the friction force between spherical glass probes of different radii of curvature (R=1.65 mm, 3.40 mm, 6.05 mm, 7.75 mm, 12.84 mm, and 18.75 mm) and a porous PDMS sample. At least three trials were run for each probe radius. The PDMS sample included pores having a diameter of 40 µm and a depth of 30 µm. The pores were separated by 20 µm and arranged in a square lattice. Water was the lubricant in this example. In all cases, a preload of 98 mN was applied and the surfaces were sheared at a constant velocity of 0.40 mm/s. The friction force started out relatively high when using a probe with a small radius of curvature, but then dropped rapidly as the probe radius increased. A local maximum in the force curve was found when using a probe with a radius of curvature of 7.75 mm followed by another gradual drop in the friction force as the probe radius was further increased. We can explain this behavior in the friction force by considering an interplay between boundary and hydrodynamic lubrication, primarily dictated by the applied pressure at the contact region.

Three domains (labeled (i), (ii), and (iii) in FIG. 12) were proposed based on the resulting pressure exerted at the glass/PDMS interface. Since the applied normal force is kept constant throughout each experiment, the applied pressure and the area of contact changed depending on the radius of curvature of the probe. The probe with the smallest radius of curvature (R=1.65 mm) exhibited the largest contact pressure. We propose that at such large pressures, the projections deform significantly, thereby closing the pore openings. The pressure was also sufficiently large to completely or partially squeeze out interfacial water present in the contact region, resulting in a boundary lubrication dominated regime (see domain (i) in FIG. 12).

As the radius of curvature of the probe is increased, the applied pressure decreased. In domain (ii), the pressure was sufficiently large to allow for the LIHL regime to dominate and, thus, pressurized water was expelled from the pores separating the shearing surfaces. We can explain the slight increase in the friction force when using larger probe radii by the fact that the applied pressure decreased, resulting in lower projection deformation. Since less water escaped from the pores, the shearing surfaces made partial true contact resulting in mixed boundary lubrication. Consequently, in domain (ii) the contact pressure which would normally be sufficient to expel fluid from the contact region and cause the shearing surface to make true contact is balanced by the pressurized extrusion of water from the pores, resulting in the LIHL mechanism.

Further increasing the radius of curvature of the probe caused the contact pressure to further decrease. The low pressure was not sufficient to squeeze out water present in the contact region and the pores containing water acted as fluid reservoirs. As a result, we again enter a hydrodynamic lubrication dominated regime in domain (iii), but different from LIHL.

Figure 13:
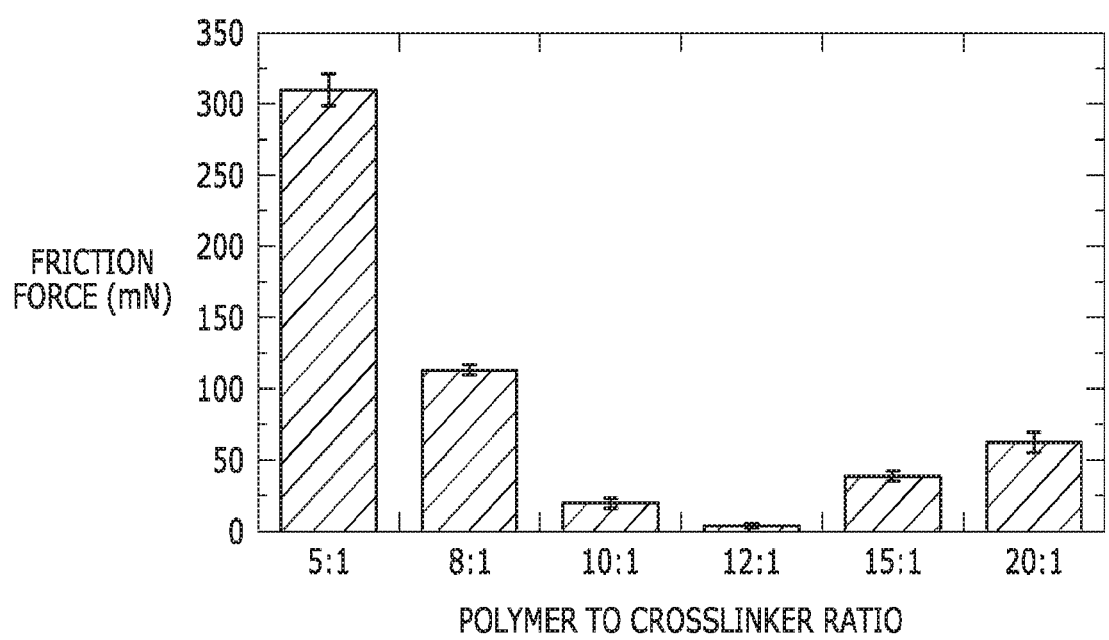
FIG. 13 is a plot of the average friction force between porous PDMS samples having different compressibility.

FIG. 13 is a plot of the average friction force between porous PDMS samples of different compressibility made by changing the ratio of PDMS to crosslinker when sheared against a glass probe (R=7.75 mm) under water. The elastic modulus of Sylgard 184 PDMS can be varied by changing the ratio of polymer to cross-linker; higher crosslinker weight fractions lead to PDMS samples with higher elastic moduli and vice versa. Polymer to crosslinker ratios from 5:1, 8:1, 10:1, 12:1, 15:1 and 20:1 were used to create the porous PDMS samples. The shear velocity was 0.40 mm/s and the applied load was 98 mN.

The friction force data as a function of the PDMS to crosslinker ratio follows a bell-shaped curve. In the case of a relatively stiff polymer, i.e., 5:1 polymer to crosslinker ratio, having a Young's Modulus of about 2.8 MPa, the applied load was insufficient to cause adequate projection deformation. Boundary lubrication dominated in this case and water was continuously squeezed out of the contact zone, resulting in high friction. As the Young's Modulus of the porous PDMS sample was decreased by increasing the PDMS-to-crosslinker ratio, the resulting friction force decreased up to the 12:1 ratio, having a Young's Modulus of about 1.8 MPa). The reduced friction force was due to the softer porous PDMS samples undergoing significant elastic deformation, thereby switching from a boundary lubrication dominated regime to a LIHL (or partial LIHL) regime.

As the PDMS-to-crosslinker ratio was further increased, the friction force increased again as the PDMS sample became softer. This can be attributed to the projections undergoing significant deformation under the same load, thereby closing the pores completely as discussed in domain (i) of FIG. 11. Consequently, a pressuring fluid layer was no longer present between the shearing surfaces and therefore boundary lubrication again dominated.

Figure 14:
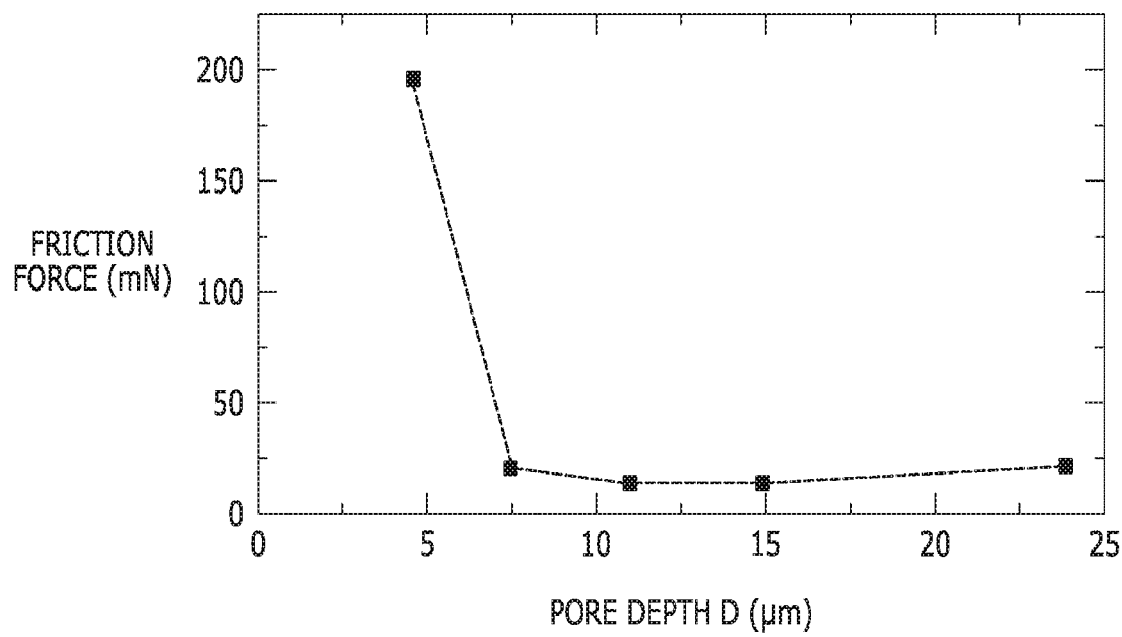
FIG. 14 is a plot of the friction force as a function of the pore depth.

The pore depth was also considered as it determines the amount of pressuring fluid that can extrude between the shearing surfaces. FIG. 14 shows a plot of the friction force as a function of the pore depth. Porous PDMS samples with pores depths (D) of 4.6 µm, 7.5 µm, 11 µm, 15 µm, and 24 µm were used in combination with a glass probe (R=7.75 mm) and water acting as the lubricant. The shear velocity was 0.40 mm/s and the applied load was 98 mN.

The friction force was found to be low and in the LIHL regime for all pore depths except D=4.6 µm. The origin of the high friction can be explained by the fact that the pores were too shallow and insufficient pressurized fluid was present to maintain a fluid layer between the shearing surfaces. Therefore, water was easily squeezed out of the contact region, leading to boundary lubrication. Once a critical pore depth was achieved, LIHL ensues, resulting in low friction. The critical pore depth is expected to be a function of the applied load and material properties of the porous polymer, which determine the extent of projection deformation.

Figure 15:
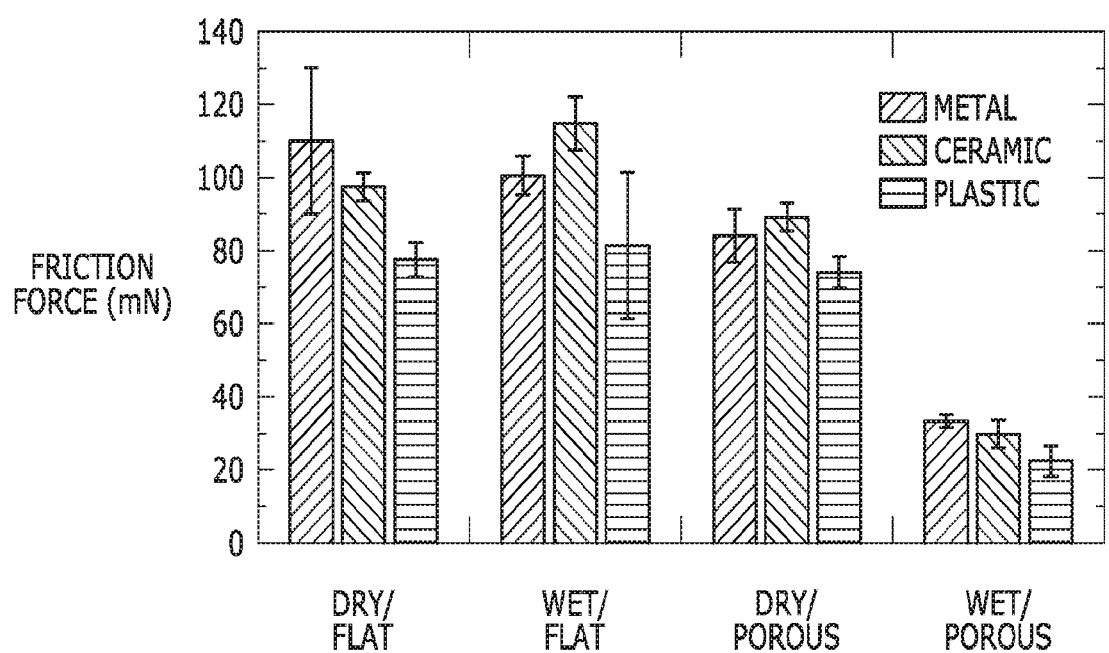
FIG. 15 is a comparison of friction forces between flat, porous PDMS samples and probes formed from different materials.

To demonstrate that the LIHL mechanism is general, PDMS samples were tested with probes made of metal (steel), ceramic (non-porous alumina) and plastic (polycarbonate) and each having a radius R of 3.18 mm. The shear velocity was 0.20 mm/s and the applied load was 49 mN. Tests were performed under four different conditions (i) flat PDMS in dry conditions; (ii) flat PDMS immersed in water; (iii) porous PDMS under dry conditions, and (iv) porous PDMS immersed in water for each probe material. FIG. 15 summarizes the results of the various test conditions.

The friction force in dry conditions was generally higher for flat PDMS samples compared to the porous PDMS samples. This can be explained by again considering the modified Amontons' law ($F=\mu L+\Gamma A$). A reduction in true area of contact A because of the addition of pores [while applying the same force F] explains the decrease in friction $\mu$ between flat and porous PDMS samples in dry conditions. However, when these samples were tested under wet conditions, the reduction in friction force $\mu$ is substantial and cannot be explained on the basis of modified Amontons' law. This study supports the conclusion that the drastic decrease in friction can be explained on the basis of load induced hydrodynamic (or mixed) lubrication. More specifically, since a pressuring fluid film maintains a separation between the shearing surfaces, our results are consistent with a LIHL mechanism, which is independent of material chemistry or potentially partially dependent in the mixed lubrication regime.

Figure 16:
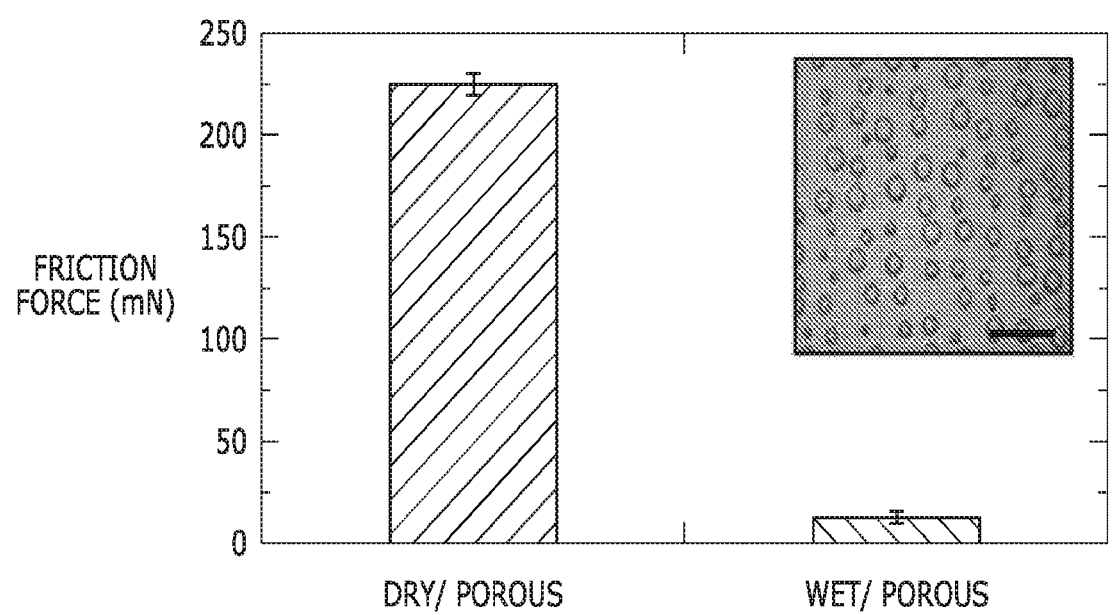
FIG. 16 is a plot of average friction force between a randomly patterned porous PDMS sample and a glass probe under dry and wet conditions.

FIG. 16 is a plot of average friction force between a randomly patterned porous PDMS sample having pores with diameters D between 10-50 µm and spaced 10-50 µm apart from one another. A glass probe (R=7.75 mm) was tested with the PDMS sample under dry and wet conditions. The shear velocity was 0.20 mm/s and the applied load was 49 mN. The inset in FIG. 16 is a top view optical image of the PDMS sample.

The sample was designed to provide a similar surface porosity as that of the patterned porous samples used in this study. Therefore, the randomly patterned porous PDMS sample was expected to have a similar effective surface modulus ensuring the same extent of pore deformation. Low friction forces were recorded, inferring that the patterned structure is not necessary as long as the effective surface modulus is in a certain range based on the applied load for LIHL to take effect.

In conclusion, key factors affecting the LIHL of porous polymers under aqueous conditions were investigated. Our results provided a deeper insight into the novel lubrication mechanism of porous compliant polymers under a localized applied load. By changing the radius of curvature of the probe and the Young's Modulus of the polymer substrate material, it was shown that the friction mechanism could shift from a boundary lubrication to a load-induced hydrodynamic lubrication regime. It is also shown that there is a desirable pore depth for observing the LIHL that is independent of material chemistry and pore pattern. Our deeper understanding of the underlying parameters that dictate the LIHL opens opportunities to design surfaces with ultra-low friction by modifying design and material properties.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A medical device for cooperating with a body surface of a patient comprising:

an elastically deformable substrate comprising hydrogel having a first surface, a second surface, and a plurality of pores extending from the first surface towards the second surface to define a plurality of projections with the pores being fluidly isolated from one another along their depth; and a lubricant comprising a non-water-soluble liquid provided in the pores;

wherein applying a compressive force to the substrate with the body surface elastically deforms the projections to displace the lubricant out of the pores and provide hydrodynamic lubrication between the medical device and the body surface.

2. The medical device recited in claim 1, wherein the projections cooperate to form a concave surface for receiving the body surface.

3. The medical device recited in claim 1, wherein the substrate is formed from a material having a Young's Modulus of about 0.1 MPa to about 100 MPa.

4. The medical device recited in claim 1, wherein the lubricant comprises an incompressible liquid having a viscosity of about $1 \times 10^{-4}$ Pa-s to about 10 Pa-s.

5. A medical device for cooperating with a body surface of a patient comprising:

an elastically deformable substrate comprising hydrogel having a first surface, a second surface, and a plurality of pores extending from the first surface towards the second surface to define a plurality of projections with the pores being fluidly isolated from one another along their depth; and a lubricant comprising at least one water-soluble liquid and at least one non-water-soluble liquid provided in the pores;

wherein applying a compressive force to the substrate with the body surface elastically deforms the projections to displace the lubricant out of the pores and provide hydrodynamic lubrication between the medical device and the body surface.

6. The medical device recited in claim 5, wherein the projections cooperate to form a concave surface for receiving the body surface.

7. The medical device recited in claim 5, wherein the substrate is formed from a material having a Young's Modulus of about 0.1 MPa to about 100 MPa.

8. The medical device recited in claim 5, wherein the lubricant comprises an incompressible liquid having a viscosity of about $1 \times 10^{-4}$ Pa-s to about 10 Pa-s.

9. A medical device for cooperating with a body surface of a patient comprising:

an elastically deformable substrate comprising hydrogel having a first surface, a second surface, and a plurality of pores extending from the first surface towards the second surface to define a plurality of projections with the pores being fluidly isolated from one another along their depth; and a lubricant comprising at least one biocompatible surface active agent including at least one phospholipid provided in the pores;

wherein applying a compressive force to the substrate with the body surface elastically deforms the projections to displace the lubricant out of the pores and provide hydrodynamic lubrication between the medical device and the body surface.

10. The medical device recited in claim 9, wherein the at least biocompatible surface active agent further comprises hyaluronic acid.

11. The medical device recited in claim 9, wherein the lubricant further comprises at least one glycerol.

12. The medical device recited in claim 9, wherein the projections cooperate to form a concave surface for receiving the body surface.

13. The medical device recited in claim 9, wherein the substrate is formed from a material having a Young's Modulus of about 0.1 MPa to about 100 MPa.

14. The medical device recited in claim 9, wherein the lubricant comprises an incompressible liquid having a viscosity of about $1 \times 10^{-4}$ Pa-s to about 10 Pa-s.

15. A medical device for cooperating with a body surface of a patient comprising:

an elastically deformable substrate comprising hydrogel having a first surface, a second surface, and a plurality of pores extending from the first surface towards the second surface to define a plurality of projections with the pores being fluidly isolated from one another along their depth; and a lubricant comprising at least one hydrogel provided in the pores;

wherein applying a compressive force to the substrate with the body surface elastically deforms the projections to displace the lubricant out of the pores and provide hydrodynamic lubrication between the medical device and the body surface.

16. The medical device recited in claim 15, wherein the lubricant further comprises at least one liquid polymer.

17. The medical device recited in claim 15, wherein the projections cooperate to form a concave surface for receiving the body surface.

18. The medical device recited in claim 15, wherein the substrate is formed from a material having a Young's Modulus of about 0.1 MPa to about 100 MPa.

19. The medical device recited in claim 15, wherein the lubricant comprises an incompressible liquid having a viscosity of about $1 \times 10^{-4}$ Pa-s to about 10 Pa-s.

* * * * *